(12) United States Patent
Hauser

(10) Patent No.: US 10,799,331 B2
(45) Date of Patent: Oct. 13, 2020

(54) SYSTEM FOR REMOVING A THROMBUS FROM A BLOOD VESSEL

(71) Applicant: David L Hauser, Newport Beach, CA (US)

(72) Inventor: David L Hauser, Newport Beach, CA (US)

(*) Notice: Subject to any disclaimer, the term of this patent is extended or adjusted under 35 U.S.C. 154(b) by 176 days.

(21) Appl. No.: 16/030,622

(22) Filed: Jul. 9, 2018

(65) Prior Publication Data
US 2018/0325647 A1   Nov. 15, 2018

Related U.S. Application Data

(63) Continuation of application No. 15/834,869, filed on Dec. 7, 2017, now Pat. No. 10,016,266, which is a continuation of application No. 14/623,425, filed on Feb. 16, 2015, now Pat. No. 9,848,975, which is a continuation of application No. 13/597,118, filed on Aug. 28, 2012, now Pat. No. 8,956,386, which is a continuation of application No. 12/749,233, filed on Mar. 29, 2010, now Pat. No. 8,252,020, which is a
(Continued)

(51) Int. Cl.
*A61M 29/00* (2006.01)
*A61F 2/01* (2006.01)
*A61B 17/221* (2006.01)
*A61B 17/225* (2006.01)
*A61B 17/22* (2006.01)
*A61B 17/3207* (2006.01)

(52) U.S. Cl.
CPC .............. *A61F 2/01* (2013.01); *A61B 17/221* (2013.01); *A61B 17/225* (2013.01); *A61B 17/22012* (2013.01); *A61B 17/320758* (2013.01); *A61F 2/013* (2013.01); *A61B 2017/22001* (2013.01); *A61B 2017/2212* (2013.01); *A61B 2017/320775* (2013.01); *A61F 2002/016* (2013.01); *A61F 2002/018* (2013.01); *A61F 2230/0006* (2013.01); *A61F 2230/006* (2013.01); *A61F 2230/008* (2013.01); *A61F 2230/0067* (2013.01); *A61F 2230/0093* (2013.01)

(58) Field of Classification Search
CPC ................ A61B 17/221; A61B 17/225; A61B 17/320758; A61F 2/01; A61F 2/13
See application file for complete search history.

(56) References Cited

U.S. PATENT DOCUMENTS

| 4,643,184 A | 2/1987 | Mobin-Uddin |
| 4,776,337 A | 10/1988 | Palmaz |

(Continued)

*Primary Examiner* — Tuan V Nguyen

(57) ABSTRACT

A system for mechanically capturing and removing a thrombus from a blood vessel includes a flexible guidewire adapted to contact the thrombus in the blood vessel, an aspiration catheter, an elongate catheter, and a self-expanding body fixedly attached to a distal end portion of the elongate catheter. The self-expanding body extends distally from the elongate catheter for capturing the thrombus. The self-expanding body preferably has a proximal end portion with a tapered shape and an open distal end. The self-expanding body is permeable for allowing blood to pass through the self-expanding body and into the central lumen of the aspiration catheter. The system may further include a thrombolytic drug to help dissolve the thrombus before capturing the thrombus with the self-expanding body.

17 Claims, 10 Drawing Sheets

Related U.S. Application Data continuation of application No. 10/594,198, filed as application No. PCT/US2005/010160 on Mar. 25, 2005, now Pat. No. 7,686,825.

(60) Provisional application No. 60/556,152, filed on Mar. 25, 2004.

(56) References Cited

U.S. PATENT DOCUMENTS

| | | | |
|---|---|---|---|
| 4,790,812 A | 12/1988 | Hawkins, Jr. et al. | |
| 4,870,953 A | 10/1989 | DonMicheal et al. | |
| 4,873,978 A | 10/1989 | Ginsburg | |
| 4,886,062 A | 12/1989 | Wiktor | |
| 4,898,575 A | 2/1990 | Fischell et al. | |
| 5,011,488 A | 4/1991 | Ginsburg | |
| 5,370,653 A | 12/1994 | Cragg | |
| 5,456,667 A | 10/1995 | Ham et al. | |
| 5,496,365 A | 3/1996 | Sgro | |
| 5,527,326 A | 6/1996 | Hermann et al. | |
| 5,549,626 A | 8/1996 | Miller et al. | |
| 5,769,816 A | 6/1998 | Barbut et al. | |
| 5,800,457 A * | 9/1998 | Gelbfish | A61F 2/01 606/200 |
| 5,860,938 A | 1/1999 | Lafontaine et al. | |
| 5,895,406 A | 4/1999 | Gray et al. | |
| 5,911,733 A | 6/1999 | Parodi | |
| 5,911,754 A | 6/1999 | Kanesaka et al. | |
| 5,954,737 A | 9/1999 | Lee | |
| 6,030,397 A | 2/2000 | Monetti et al. | |
| 6,066,149 A | 5/2000 | Samson et al. | |
| 6,068,645 A * | 5/2000 | Tu | A61B 18/1492 606/159 |
| 6,142,987 A | 11/2000 | Tsugita | |
| 6,146,396 A | 11/2000 | Konya et al. | |
| 6,146,403 A | 11/2000 | St Germain | |
| 6,159,230 A | 12/2000 | Samuels | |
| 6,165,200 A * | 12/2000 | Tsugita | A61F 2/01 606/200 |
| 6,179,859 B1 | 1/2001 | Bates et al. | |
| 6,203,561 B1 | 3/2001 | Ramee et al. | |
| 6,245,089 B1 | 6/2001 | Daniel et al. | |
| 6,322,572 B1 | 11/2001 | Lee | |
| 6,361,545 B1 | 3/2002 | Macoviak et al. | |
| 6,402,771 B1 | 6/2002 | Palmer et al. | |
| 6,454,775 B1 | 9/2002 | Demarais et al. | |
| 6,458,139 B1 | 10/2002 | Palmer et al. | |
| 6,475,236 B1 | 11/2002 | Roubin et al. | |
| 6,485,502 B2 | 11/2002 | Don Michael et al. | |
| 6,508,782 B1 | 1/2003 | Evans et al. | |
| 6,530,923 B1 | 3/2003 | Dubrul et al. | |
| 6,544,276 B1 | 4/2003 | Azizi | |
| 6,575,995 B1 | 6/2003 | Huter et al. | |
| 6,610,077 B1 | 8/2003 | Hancock et al. | |
| 6,620,148 B1 | 9/2003 | Tsugita | |
| 6,635,070 B2 | 10/2003 | Leeflang et al. | |
| 6,660,014 B2 | 12/2003 | Demarais et al. | |
| 6,702,830 B1 | 3/2004 | Demarais et al. | |
| 6,790,204 B2 | 9/2004 | Zadno-Azizi et al. | |
| 6,824,545 B2 | 11/2004 | Sepetka et al. | |
| 6,824,550 B1 | 11/2004 | Noriega et al. | |
| 6,945,977 B2 | 9/2005 | Demarais et al. | |
| 7,063,707 B2 | 6/2006 | Bose et al. | |
| 7,220,269 B1 | 5/2007 | Ansel et al. | |
| 7,300,458 B2 | 11/2007 | Henkes et al. | |
| 8,608,754 B2 | 12/2013 | Wensel et al. | |
| 2001/0044598 A1* | 11/2001 | Parodi | A61M 25/1027 604/104 |
| 2002/0016564 A1* | 2/2002 | Courtney | A61B 17/22 604/96.01 |
| 2002/0049452 A1 | 4/2002 | Kurz et al. | |
| 2002/0173819 A1 | 11/2002 | Leeflang et al. | |
| 2002/0188276 A1 | 12/2002 | Evans et al. | |
| 2005/0085846 A1 | 4/2005 | Carrison et al. | |
| 2007/0093744 A1 | 4/2007 | Elmaleh | |

* cited by examiner

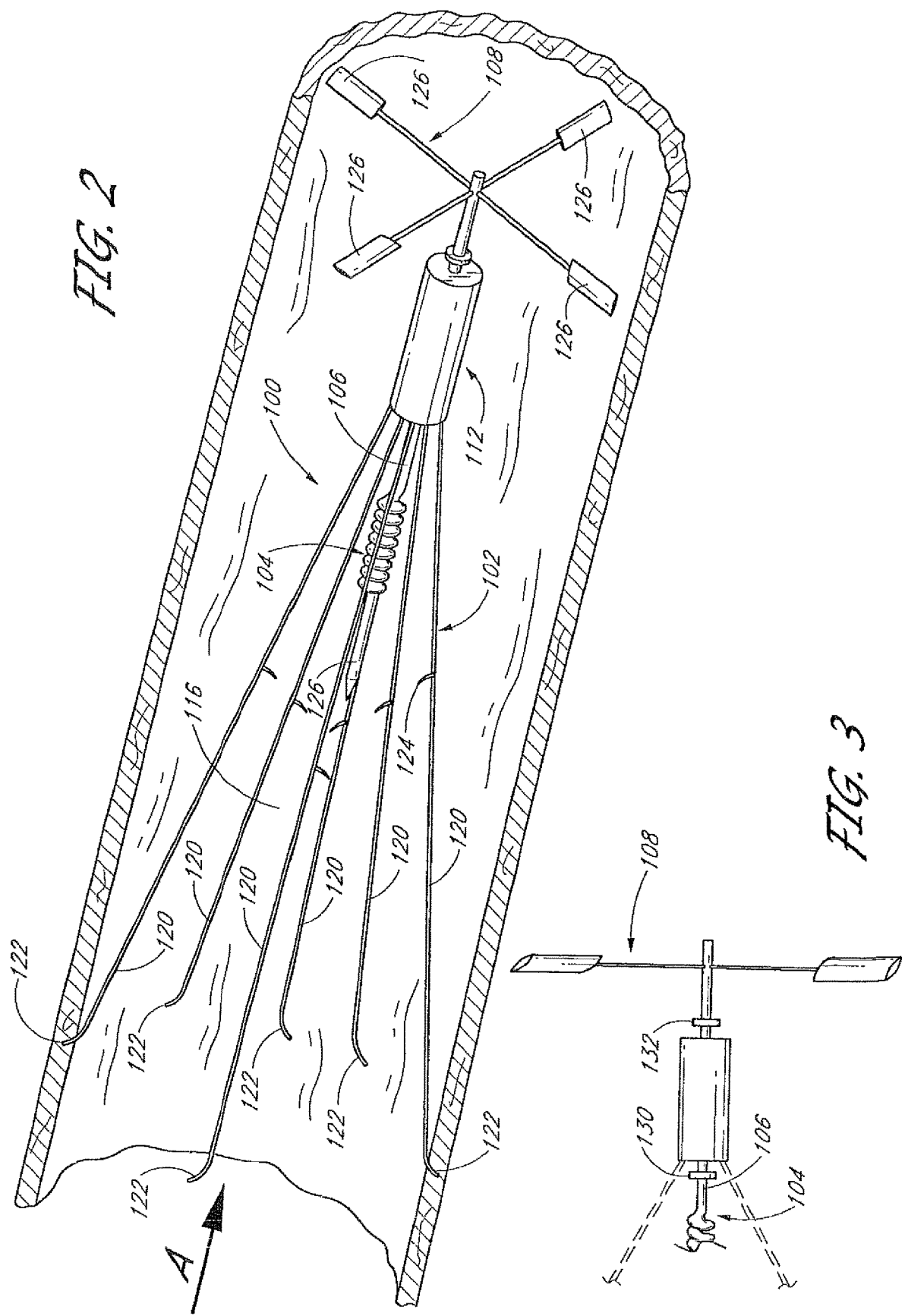

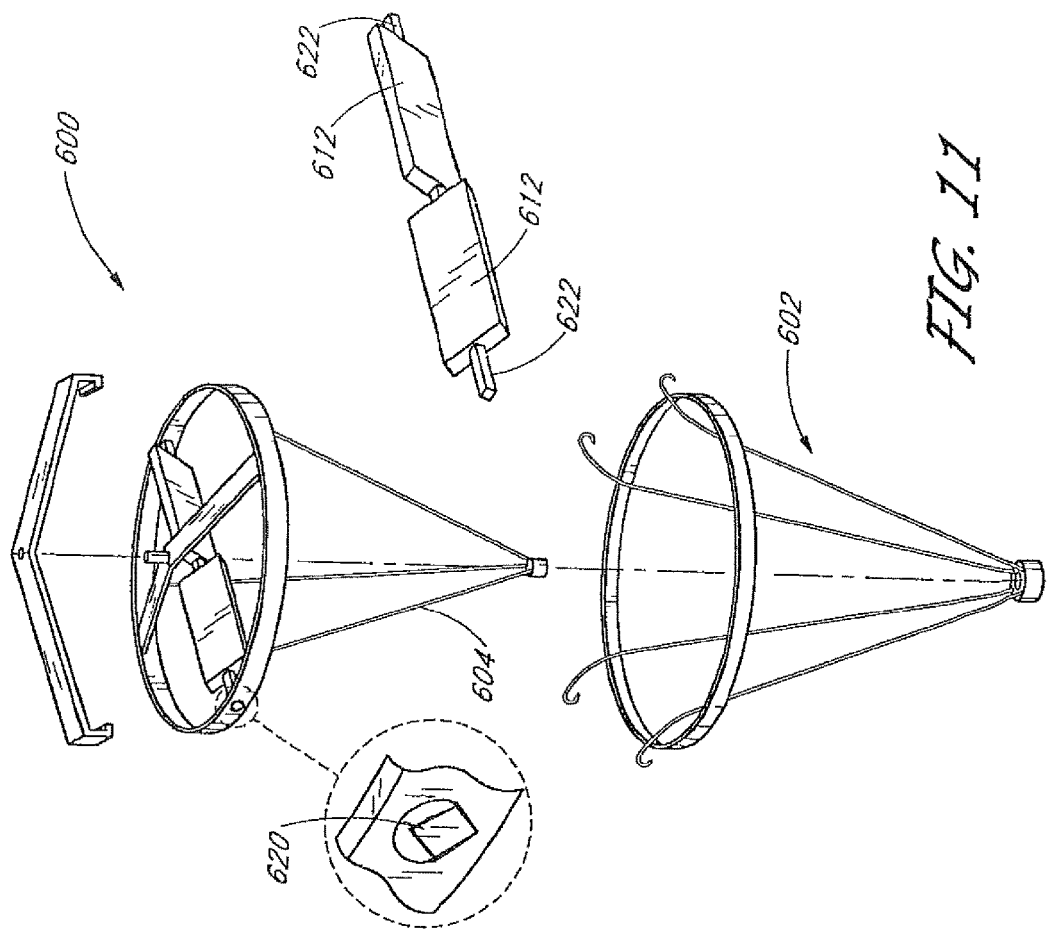
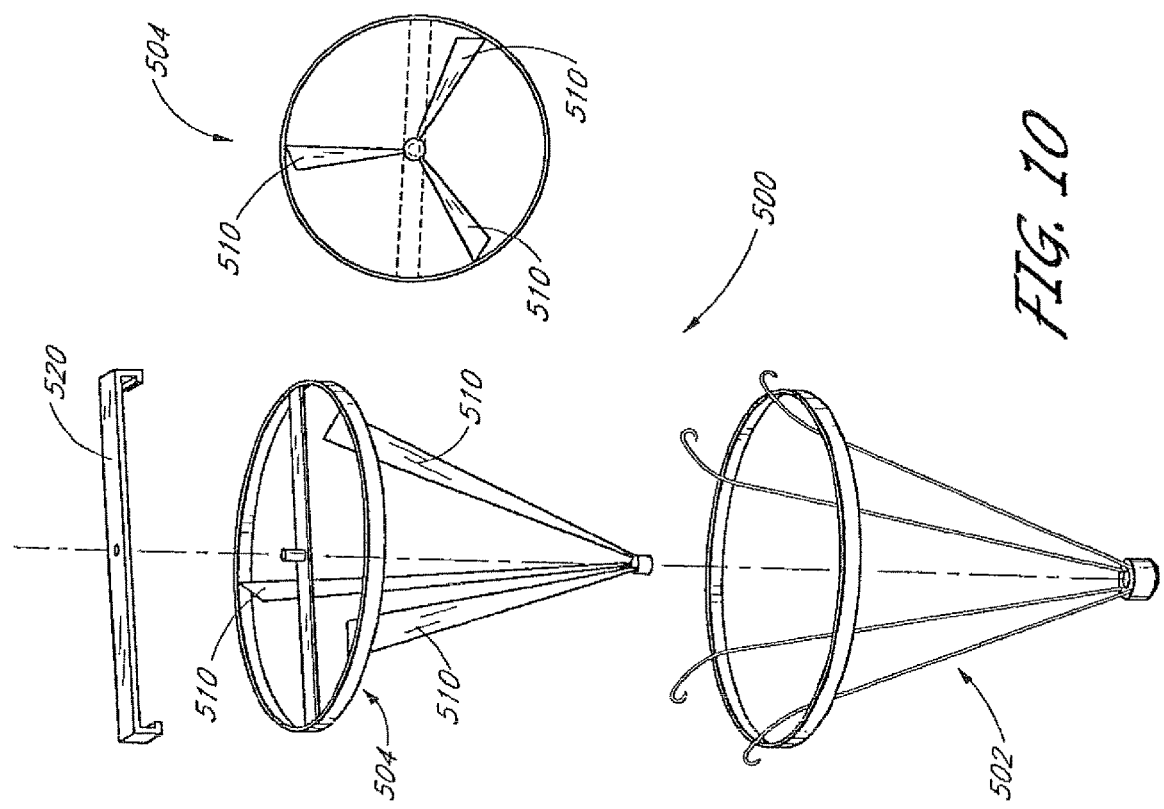
FIG. 11
FIG. 10

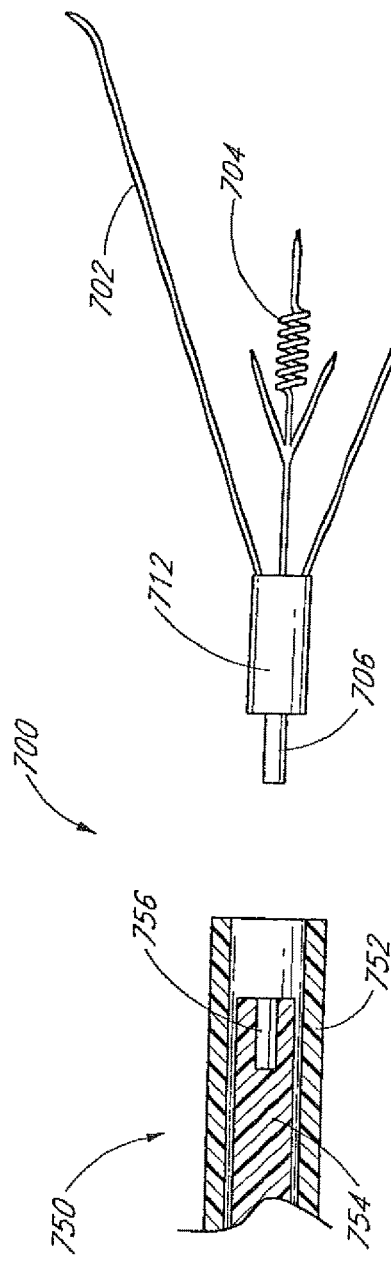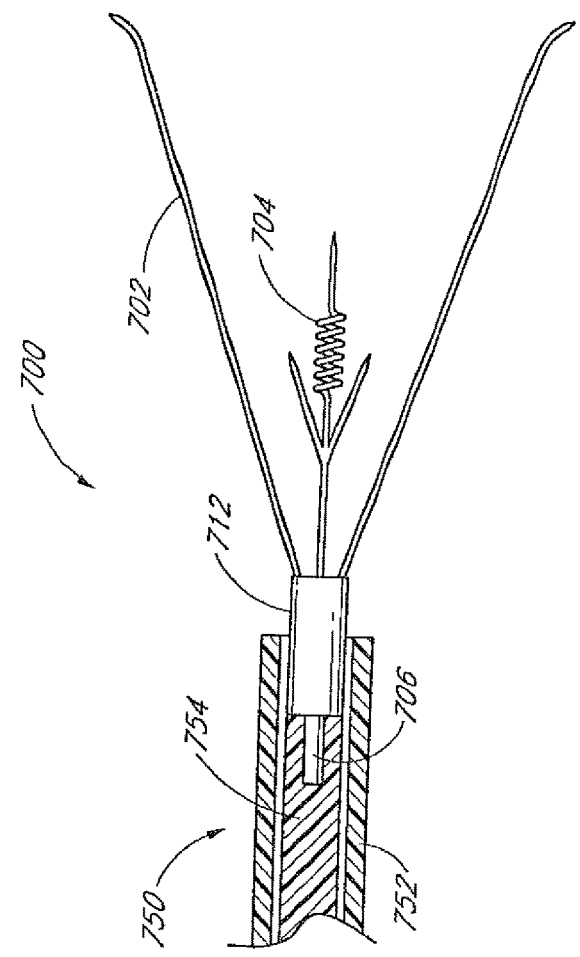
FIG. 12
FIG. 12A

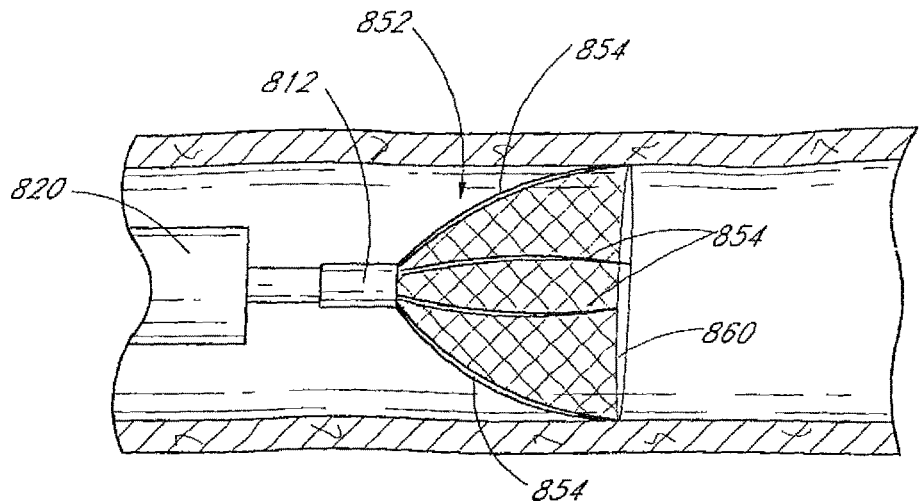
FIG. 16
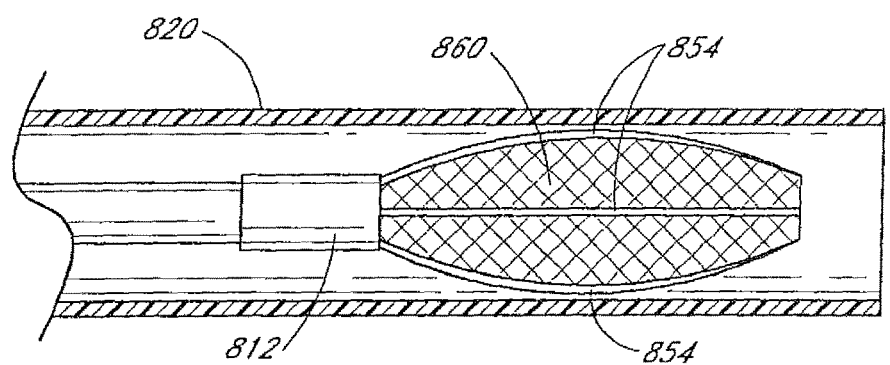
FIG. 16A
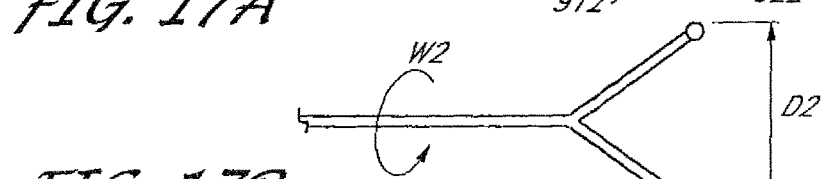
FIG. 17A
FIG. 17B
FIG. 17C

SYSTEM FOR REMOVING A THROMBUS FROM A BLOOD VESSEL

RELATED APPLICATIONS

The present application is a continuation of U.S. application Ser. No. 15/834,869, filed Dec. 7, 2017, now U.S. Pat. No. 10,016,266, which is a continuation of U.S. application Ser. No. 14/623,425, filed Feb. 16, 2015, now U.S. Pat. No. 9,848,975, which is a continuation of U.S. application Ser. No. 13/597,118, filed Aug. 28, 2012, now U.S. Pat. No. 8,956,386, which is a continuation of U.S. application Ser. No. 12/749,233, filed Mar. 29, 2010, now U.S. Pat. No. 8,252,020, which is a continuation of U.S. application Ser. No. 10/594,198, filed Sep. 25, 2006, now U.S. Pat. No. 7,686,825, which is a National Phase Application of International Application No. PCT/US2005/010160, filed Mar. 25, 2005, which designates the United States and was published in English by the International Bureau on Oct. 13, 2005 as WO 2005/094283 A2 and which claims the benefit of priority of U.S. Provisional Application No. 60/556,152, filed Mar. 25, 2004. Each of the above-referenced applications is hereby incorporated by reference in its entirety.

BACKGROUND OF THE INVENTION

Field of the Invention

The present invention relates generally to medical devices and, more particularly, the invention relates to a filter device that is adapted to capture and remove particles from a body lumen.

Description of the Related Art

Vascular filters are used in a wide variety of applications wherein it is desirable to capture particles from the blood. One primary use of vascular filters is for protecting against a condition called pulmonary embolism (PE). A pulmonary embolism occurs when a blood clot (embolus) or other particle in the cardio-pulmonary blood circulation creates a pulmonary arterial blockage. A pulmonary embolism can be a life-threatening condition because the clot may effectively cut off the body's oxygen supply. To reduce the likelihood of this event, a vascular filter may be implanted within a blood vessel, such as the inferior vena cava or other large vein, for capturing blood clots before they can reach the pulmonary vasculature. The use of vascular filters has been particularly useful for treating patients suffering from deep vein thrombosis (DVT), a condition wherein a blood clot (thrombus) can form in a leg and then break free (now an embolus) and migrate into the cardio-pulmonary vasculature.

Delivery of a vascular filter to a blood vessel is usually achieved through a peripheral vein access site, such as, for example, the jugular or femoral veins. One of the earliest examples of a vascular filter is the Mobin-Uddin ("MU") umbrella filter, which was developed in 1967. The MU filter provided an alternative to a variety of treatment techniques, such as surgical ligation, caval plication, and caval clips, which were used at the time for treating venous stasis and preventing PE. The MU filter is composed of six flat Elgiloy spokes radiating from a hub and partially covered by a web designed to capture blood clots. MU filters were typically introduced into the body via a cutdown of the jugular or femoral vein and subsequent passing of a catheter through the access site to the filter implant site in the infrarenal inferior vena cava.

In 1973, Greenfield et al. introduced a new stainless steel filter. This type of filter is conical in shape and is composed of six equally spaced stainless steel wires. The filter is adapted to hold a clot in the infrarenal vena cava until the body's own lytic system dissolves the clot. Since the introduction of the original Greenfield filter, subsequent derivatives have been developed to reduce the size of the introducer catheter for facilitating percutaneous introduction. For example, in 1989, the Titanium Greenfield Filter (TGF) was introduced as a low-profile system to facilitate the ease of percutaneous insertion.

Still other vena cava filters were introduced in the United States in the late 1980s, including the Vena Tech-LGM vena cava filter, the Bird's Nest vena cava filter, and the Simon-Nitinol vena cava filter. The Vena Tech-LGM filter is a conical filter made from a Phynox alloy, with longitudinal stabilizing legs in addition to the intraluminal cone. The Bird's Nest filter is a "nest" of stainless steel wire which is wound into the vena cava, while the Simon Nitinol filter is a two-stage filter made from nickel-titanium (NiTi) alloy with a conical lower section and a petal-shaped upper section. The TrapEase filter is yet another filter that was approved by the FDA in the summer of 2000. The TrapEase filter is laser cut from a single tube of Nitinol material and is formed with a symmetric double-basket configuration providing two levels of clot trapping.

Although vascular filters are widely used for capturing emboli in blood vessels, existing filter configurations suffer from a variety of shortcomings that limit their effectiveness. In one primary shortcoming, vascular filters are susceptible to clogging with embolic material. When a filter becomes partially or totally clogged, the flow of blood through the vessel may be substantially reduced or stopped completely. When this occurs, serious complications can arise and therefore the patient must be treated immediately to restore adequate blood flow. Because of the potential for clogging, existing vascular filters are typically manufactured with relatively large pores or gaps such that only large emboli, such as those with diameters of 7 mm or greater, are captured. The large pore size is necessary for reducing the likelihood of clogging due to smaller particles. Unfortunately, in certain cases, the passage of smaller emboli may still be capable of causing a pulmonary embolism or stroke. Accordingly, physicians and filter manufacturers are required to balance the risk of clogging against the risk of pulmonary embolism and/or stroke.

Catheter-based mechanical thrombectomy devices provide an alternative treatment method for removing blood clots from a patient's vasculature. Thrombectomy devices are typically used for removing a thrombus that has formed in a blood vessel and has occluded the flow of blood. Existing thrombectomy devices include the Oasis™ Thrombectomy System by Boston Scientific, the Hydrolyser™ by Cordis, the Helix™ Clot Buster® by ev3/Microvena, the Arrow Trerotola PTD™ kit by Arrow International, the MTI-Cragg Brush™ by MicroTherapeutics, the Angiojet Xpeedior™ 100 Catheter by Possis, and the Thrombex PMT™ system by Edwards Lifesciences.

Thrombectomy devices have gained popularity in recent years as experience with the devices has increased. However, the use of these devices can be cumbersome, time-consuming and expensive. Furthermore, these devices do not capture emboli in the blood. Rather, these devices are used to remove a thrombus that has formed within a vessel.

In certain cases, these devices may actually produce emboli and cause a stroke or PE. Still further, the contact surfaces or fluid pressures of these mechanical thrombectomy devices may produce a variety of undesirable side-effects, such as endothelial denudation and hemolysis. Finally, these devices have not yet proven to be sufficiently mechanically reliable for widespread use.

Therefore, due to the numerous shortcomings associated with existing vascular filters and thrombectomy devices, an urgent need exists for improved devices and methods for capturing and removing blood clots from a patient's vasculature. The present invention addresses this need.

SUMMARY OF THE INVENTION

The present invention provides a vascular filter device adapted for capturing and breaking down embolic material from the blood.

Preferred embodiments of the present invention generally comprise a filter body sized for deployment in a blood vessel, and an agitation member movably coupled to the filter body. During use, movement of the agitation member acts to break apart particles captured within the filter body. To reduce the possibility of filter migration, the filter body may be provided with anchoring elements for engagement with an inner wall of the blood vessel. The anchoring elements may comprises penetrating tips, barbs, hooks or any other structure configured to engage the inner wall. In another variation, the filter device may be supported by a stent structure that expands for engagement with the inner wall.

The filter body preferably comprises a plurality of elongate legs coupled together at one end to form a substantially conically-shaped body having an interior volume configured for capturing emboli. The vascular filter is preferably configured to be collapsible for delivery to a treatment site. In one variation, the vascular filter is self-expanding. In another variation, the vascular filter is balloon expandable. The filter body is coated with an anti-coagulent material.

In one aspect, the agitation member is rotatably coupled to the filter body. A flow-receiving member may be provided for causing the agitation member to rotate relative to the filter body. In one variation, the agitation member is capable of reversing direction during use. If desired, the vascular filter may further comprise a clutch mechanism such that the agitation member only rotates relative to the filter body when a particle is trapped within the filter body. To further enhance the dissolution of particles trapped within the filter body, the filter body may further comprise inwardly protruding members that cooperate with the agitation member to break down the particle.

In another variation, movement of the agitation mechanism may be provided by an elongate drive mechanism. The elongate drive mechanism may be removably attachable to the agitation member or the components may be provided as a single unit. The drive mechanism preferably includes a rotatable inner catheter contained within an outer catheter. The outer catheter couples to the filter body and remains rotationally fixed. The inner catheter couples to the agitation member and causes the agitation member to rotate.

In another aspect, the agitation member is configured to vibrate within the filter body. In one preferred embodiment, the agitation member vibrates at ultrasonic frequencies.

In another aspect, the agitation member is configured to emit a pressurized flow of fluid for producing hydrodynamic forces for breaking apart a clot.

In another aspect, the vascular filter further comprises an energy storage device coupled to the agitation member for producing movement of the agitation member.

Preferred embodiments of the present invention also provide a method of making a vascular filter. In one embodiment, the method comprises providing a filter body sized for capturing particles from the blood and coupling an agitation member to the filter body, wherein the agitation member is rotatable relative to the filter body.

Preferred embodiments of the present invention also provide a method of filtering particles from blood in a blood vessel, comprising providing a vascular filter having a filter body and an agitation member movably coupled to the filter body. The method further comprises collapsing the vascular filter, inserting the vascular filter into a lumen of a delivery catheter, introducing the delivery catheter into the blood vessel, and deploying the vascular filter from a distal end of the delivery catheter at a desired location within the blood vessel. After delivery, captured particles are broken apart by causing the agitation member to move relative to the filter body.

BRIEF DESCRIPTION OF THE DRAWINGS

FIG. 2 is a side view illustrating an improved vascular filter according to one preferred embodiment of the present invention.

FIG. 3 is an enlarge view illustrating the cooperation between the shaft portion and the hub of the vascular filter of FIG. 2.

FIG. 10 illustrates another alternative embodiment of a vascular filter device wherein a flow-receiving member comprises vanes extending parallel to the filter body.

FIG. 11 illustrates another alternative embodiment of a vascular filter device wherein the agitation member is capable of reversing direction.

FIG. 12 illustrates another alternative embodiment of a vascular filter device further comprising an elongate drive mechanism, the drive mechanism being removably attachable to the filter device.

FIG. 12A illustrates the vascular filter device of FIG. 12 with the elongate drive mechanism coupled to the filter body for driving the agitation member.

FIGS. 16 and 16A illustrate an alternative filter body embodiment having stiffened members for creating an enclosed volume when withdrawn into a delivery sheath.

FIGS. 17A through 17C illustrate an alternative agitation member having a controllable diameter.

DETAILED DESCRIPTION OF THE PREFERRED EMBODIMENTS

Preferred embodiments of the present invention provide improved devices and methods for capturing and dissolving blood clots within a patient's vasculature. In one important embodiment, the present invention provides an implantable mechanical device that is powered by the flow of blood through a blood vessel. Embodiment of the present invention may be used to capture and dissolve a wide variety of particles. As a result, embodiments of the present invention may be used to improve circulation and reduce the chance of clot-related health problems, such as stroke and pulmonary embolism.

Figure 1:
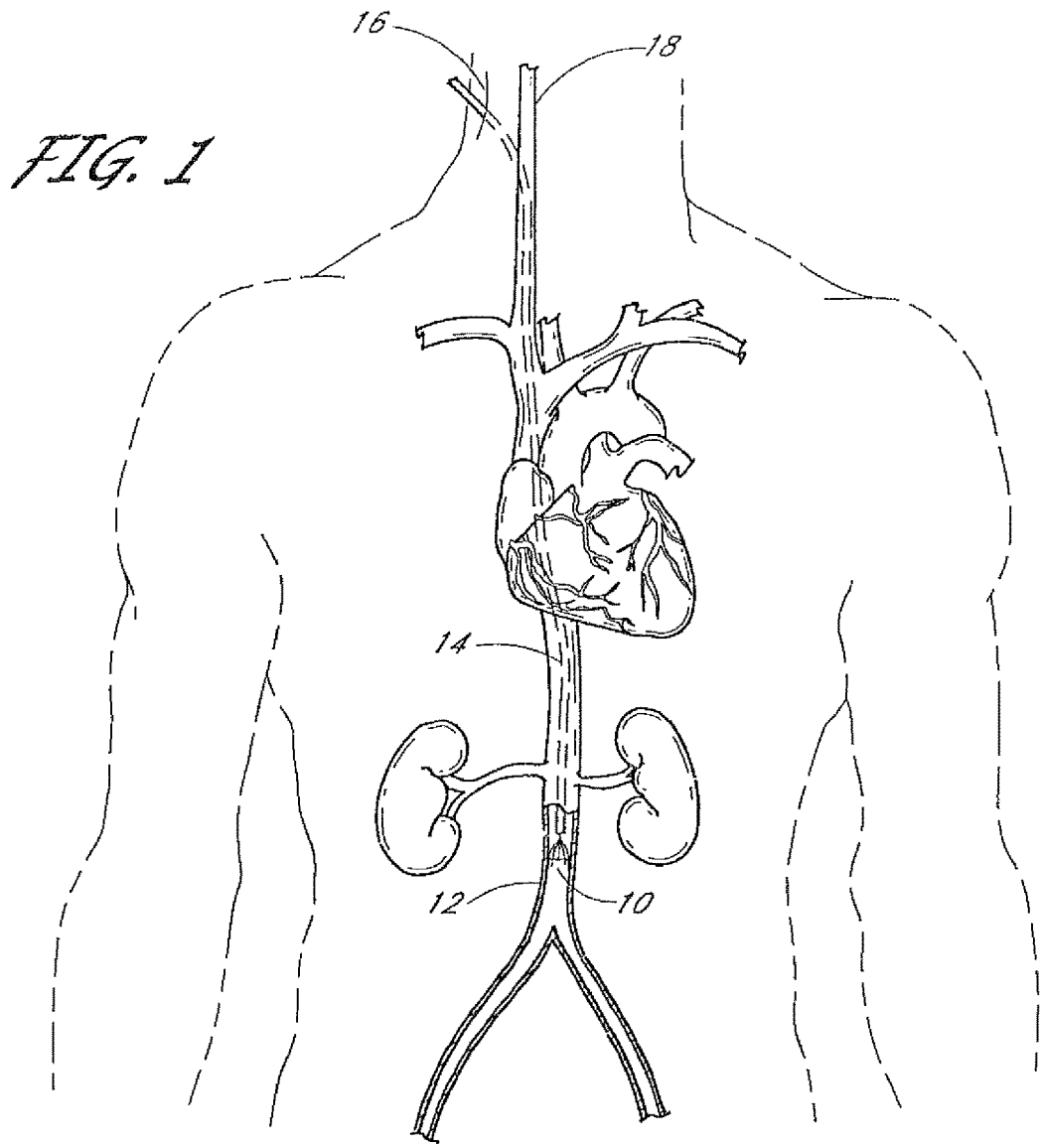
FIG. 1 illustrates one method of deploying a filter device in a blood vessel for capturing emboli.
Figure 1A:
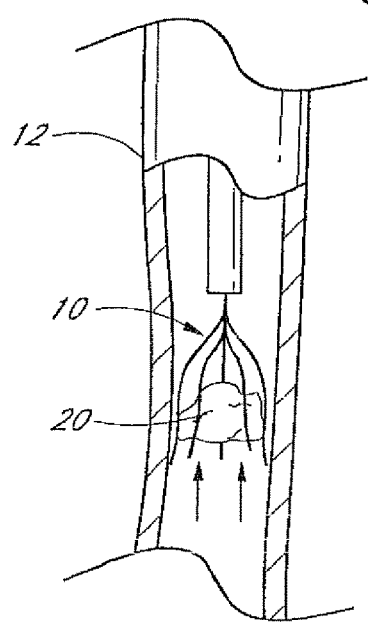
FIG. 1A illustrates the filter device of FIG. 1 after capturing a large embolus.

Referring to FIG. 1, for background purposes, a filter device 10 for filtering particles from the blood is illustrated. The filter device is shown during implantation in the inferior vena cava 12. The filter device 10 is delivered to a treatment site through a catheter 14. The delivery catheter 14 is inserted through an access site 16 adjacent the jugular vein. With reference now to FIG. 1A, the filter device 10 is shown with a large blood clot 20 captured therein. The filter device is configured to hold the captured clot until the body's natural lytic system causes the clot to dissolve. However, as can be seen in FIG. 1A, in one primary shortcoming of the illustrated filter device, the captured blood clot may partially or completely occlude the flow of blood through the inferior vena cava. Occlusion of the inferior vena cava can have serious consequences and therefore requires immediate medical attention.

With reference now to FIG. 2, a preferred embodiment of an improved filter device 100 is illustrated. The filter device 100 generally comprises a filter body 102 and an agitation member 104 movably coupled to the filter body. The agitation member 104 is coupled to a shaft portion 106 and a flow receiving member 108. In the illustrated embodiment, the shaft portion 110 extends through an opening in a hub 112 for rotatably coupling the agitation member to the filter body. As shown in the enlarge view of FIG. 3, regions of expanded diameter 130, 132 are provided along the shaft portion 110 at locations proximal and distal to the hub 112 for preventing the agitation member 104 from moving longitudinally with respect to the filter body 102.

The filter body 102 preferably comprises a plurality of elongate legs 120 having first and second ends. The elongate legs 120 are joined along the first ends at the hub. In a preferred embodiment, six elongate legs are provided. In the deployed condition (as shown), the elongate legs are configured to provide the filter body 102 with a substantially conical shape. The filter body 102 defines an interior volume 116 which provides an entrapment region for capturing and holding particles. The spacing between the elongate legs 120 can be configured for the particular application. However, in one preferred embodiment, the legs are spaced for capturing clots having a diameter of 7 mm or greater, while allowing smaller particles to pass therethrough. The elongate legs 120 are preferably arranged to create very little resistance to blood flow through the vessel. In one variation, one or more protruding elements 124 are provided along the inner surfaces of the elongate legs. The filter body 102 is preferably configured to be collapsible into a smaller cross-sectional profile for facilitating percutaneous delivery to a treatment site. Although the filter body is illustrated as comprising a plurality of elongated legs, the filter body may also take various alternative forms capable of capturing particles, such as, for example, a mesh or bird's nest arrangement.

One or more anchors 122 are preferably provided along the second ends of the elongate legs 120 for engaging the inner wall of the blood vessel. In various preferred embodiments, the anchors may comprise barbs, hooks or any other shape well-suited for engaging the inner wall. Preferably, the anchors are sized and configured such that they do not penetrate through the wall of the blood vessel. Over time, the anchors along the elongate legs are incorporated by endothelial tissue, thereby substantially reducing the possibility of undesirable filter migration. In another variation, the filter device may be supported by an expandable stent structure (not shown) that expands for engagement with the inner wall of the vessel. The stent may be used to help improve alignment and reduce the likelihood of undesirable filter migration.

The agitation member 104 is an elongate member having corkscrew-shaped portion. The agitation member 104 is preferably disposed within the interior volume 116 of the filter body 102. The agitation member preferably includes a pointed tip 126 adapted for engaging and penetrating a captured embolus. The agitation member is formed to break apart an embolus by producing forces which help separate the embolus into smaller pieces which can be more easily broken down by the body's natural lytic system. In other words, the agitation member provides a mechanical element for emulsifying an embolus trapped within the filter body. The agitation member preferably has a relatively small cross-sectional profile such that rotational resistance will be minimized during engagement with an embolus. Although the agitation member is illustrated as comprising a corkscrew-shaped member coupled to shaft portion and a flow receiving member, as will be described in more detail below, any movable element configured for movement within a filter body for acting on a captured particle is contemplated to fall within the scope of the present invention.

The flow receiving member 108 is coupled to the shaft portion and comprises a series of angled blades 126. The blades are configured to be acted upon by the flow of blood (shown by arrow A) for causing rotation of the shaft portion and the agitation member. The shape and arrangement of the blades is configured for producing sufficient torque to overcome resistance caused by engagement of the agitation member with the embolus.

Figure 4:
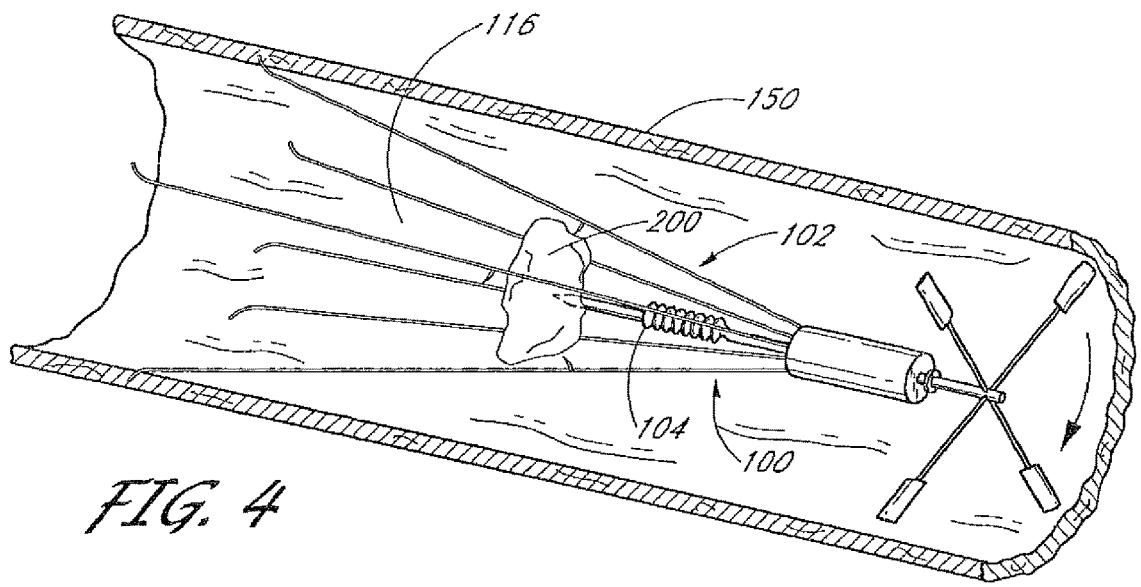
FIGS. 4 through 6 illustrate the vascular filter of FIG. 2 during use.
Figure 5:
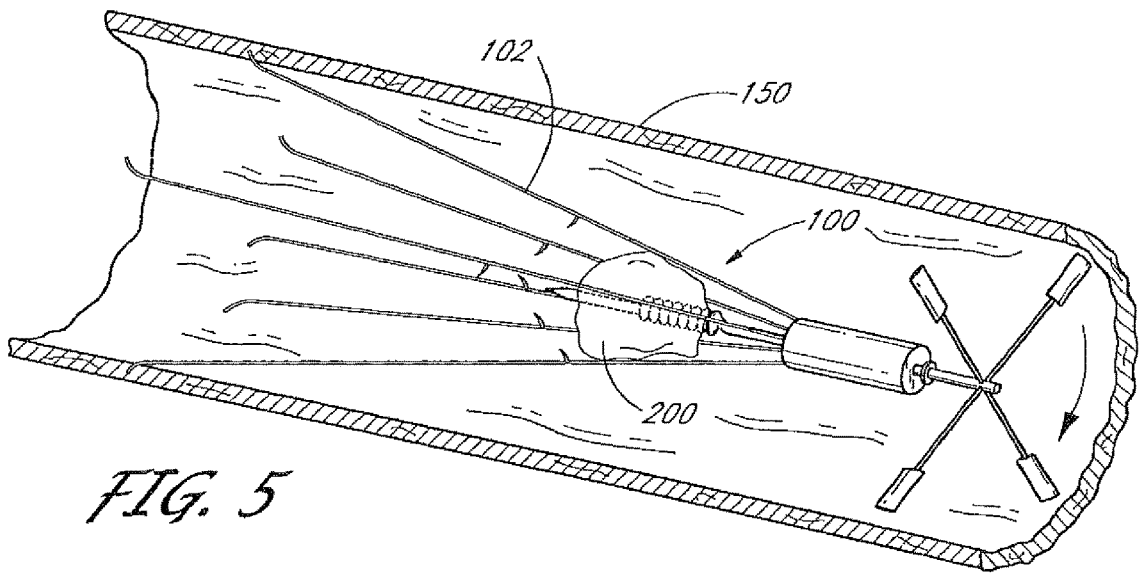
Figure 6:
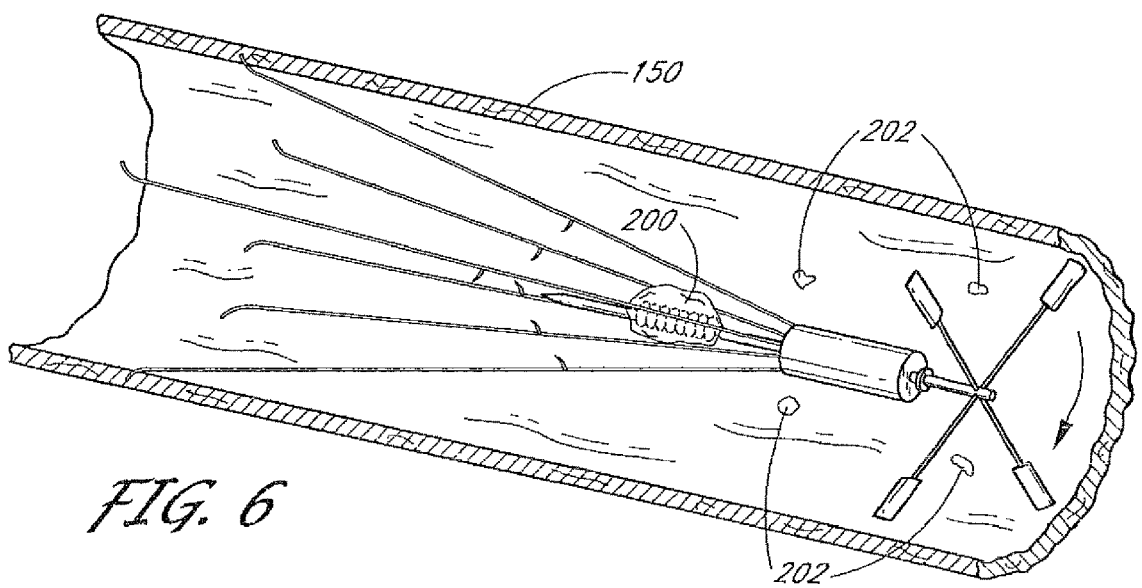

With reference now to FIGS. 4 through 6, the filter device 102 is shown during use. When an embolus 200 (or other particle in the blood) reaches the filter device 100, the embolus 200 enters the mouth of the filter body 102 and is funneled toward the center of the interior volume 116. The flow of blood pushes the embolus 200 into contact with the pointed tip of the agitation member 104, thereby causing the pointed tip to penetrate the captured embolus. Rotational movement causes the agitation member to penetrate deeper into the embolus and thereby draw the embolus further toward the apex (i.e., cephalad end) of the filter body.

With particular reference to FIG. 5, the filter device 100 is shown during use as it pulls the embolus 200 into the filter body 102. As the embolus is pulled inward, it is acted on by the protruding members 124 which help break apart the embolus. As the embolus is drawn further into the filter, pieces 202 of the embolus break away. The protruding members also prevent the embolus from rotating with the filter body, thereby ensuring that the embolus is drawn further into the filter body. When the embolus 200 reaches the apex of the filter body, as shown in FIG. 6, rotational movement of the agitation member continues to impart mechanical forces on the embolus, thereby causing it to compress and eventually dissolve into harmless smaller particles. As the embolus is broken into smaller pieces, the body's own lytic capabilities are able to quickly dissolve the remaining pieces. The remaining particles may be held within the filter body or the filter body may be configured with a pore size sufficient to allow the harmless smaller particles to pass through the filter wherein they may be dissolved downstream. It is recognized that the agitation member may not penetrate all emboli that enter the filter body. However, even if a particle enters the region between the corkscrew shaped member and the filter body, the movement of the agitation member will still act on the particle and cause it to break apart over time.

To further enhance dissolution of emboli, the vascular filter may be used in combination with one or more thrombolytic drugs. In one method, the drugs may be delivered from a catheter. The fluid pressure from the delivery of the drugs may be used to further drive the movement of the agitation member, such as by imparting forces on the flow receiving member.

Components of the filter device are preferably manufactured from biocompatible, non-corrosive materials having high fatigue strengths. In various configurations, the components of the filter device may be made of stainless steel or titanium. In another variation, some or all of the components may be made of a nickel-titanium alloy (such as Nitinol) have shape-memory properties. In one embodiment, the nickel-titanium alloy may further include Niobium for desirable material characteristics.

Components of the vascular filter device may also be coated with one or more drugs (e.g., therapeutic agents) to prevent cell growth onto or adjacent to the device. This feature helps reduce the likelihood of cell/tissue ingrowth adversely affecting the functionality of the moving parts. The therapeutic agent(s) is preferably selected from the group consisting of antiproliferative agents, anti-inflammatory, anti-matrix metalloproteinase, and lipid lowering, anti-thrombotic, and/or antiplatelet agent. In a variation, the elements of the device may contain and deliver the therapeutic agent and/or the agent may be applied to the device along certain or all surface(s) and delivered by means of a polymer or no polymer. In another alternative embodiment, the vascular filter device may include a radioactive element, such as a radioactive core, to reduce or prevent cell growth in the along the device.

Preferred embodiments of the filter device are configured to be collapsible for delivery to a treatment site. During delivery to a treatment site, the filter device is collapsed to fit within a lumen of a delivery catheter. Preferably, the filter device is self-expanding such that it expands to engage the inner surface of the vessel after delivery. The use of shape-memory materials advantageously allows the filter device components to be collapsed or crimped into a small diameter for facilitating percutaneous delivery to a treatment site, such as through a catheter or sheath. A pushing element or other deployment member may be used to expel the filter device from the sheath at the treatment site, wherein the filter expands to its desired shape.

Figure 7:
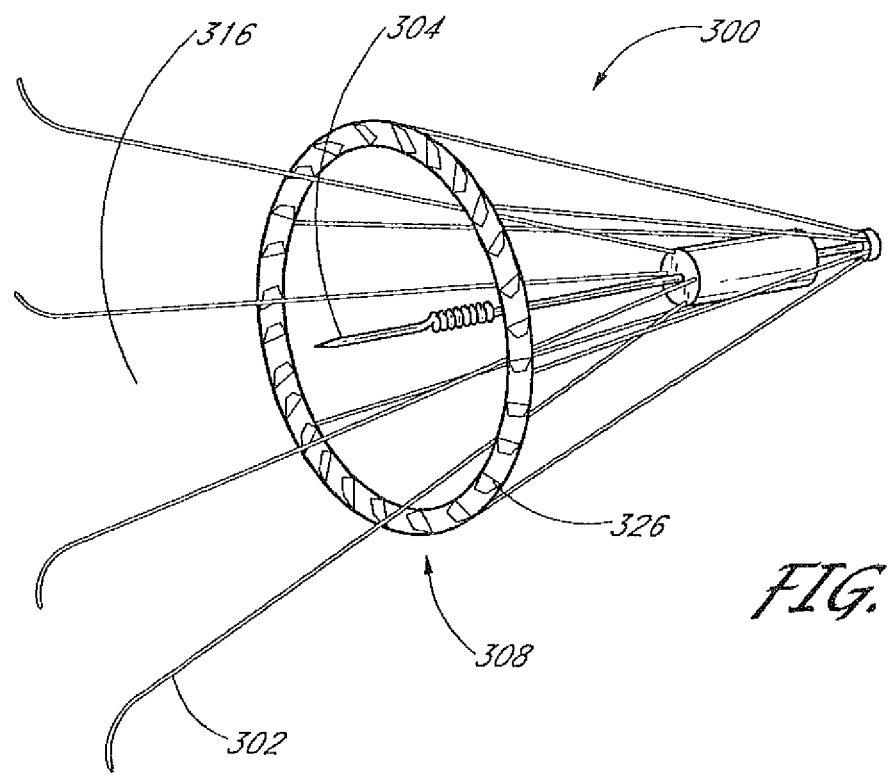
FIGS. 7 and 8 illustrate alternative embodiments of a force receiving mechanism for causing the agitation member to rotate for acting on an embolus.

With reference now to FIG. 7, a filter device 300 is shown having an alternative flow receiving member 308 configured for causing the agitation member 304 to move. In this embodiment, the flow receiving member includes an annular element 326 located around the filter body 302. It will be understood that, when an embolus is captured and held within the filter body 302, blood flows through an annular gap around the embolus. In other words, the blood is effectively channeled around the thrombus and toward the blades. Accordingly, in this embodiment, the flow rate of blood passing along the flow receiving member is advantageously increased when an embolus is trapped within the interior volume 316 of the filter body 302. As a result, the rotation of the agitation member and the available torque also increase while the embolus is captured. After the embolus has been broken down, the flow rate through the annular region decreases due to the removal of the occlusion and the resulting increased cross-sectional flow area.

Figure 8:
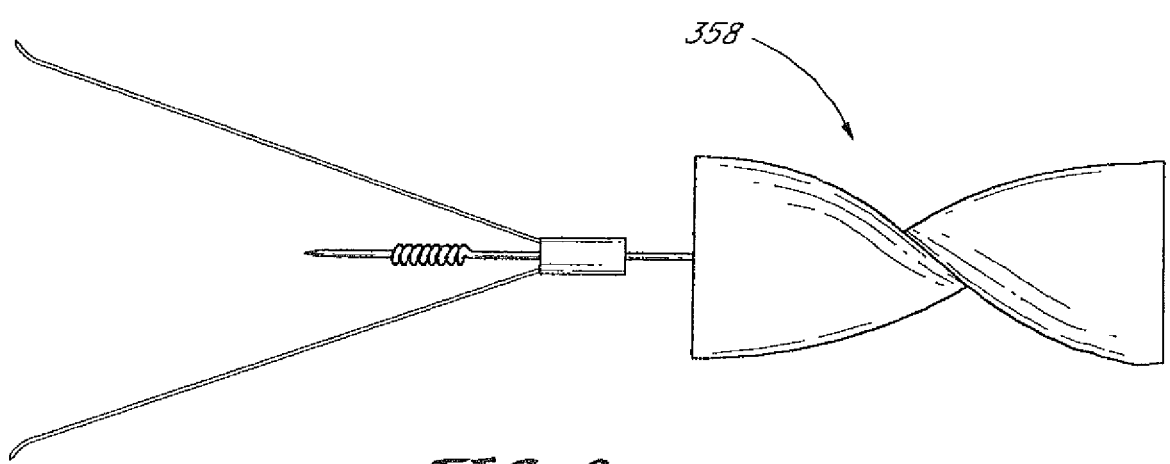

In addition to the flow receiving members illustrated and described herein, a wide variety of alternative configuration may also be used. In any case, it is desirable that the flow receiving member be configured to minimize hemolytic effects and the impedance of blood flow through the vessel. Preferably, the flow of blood should remain substantially laminar as it passes through the filter device. In alternative configurations, it is contemplated that the flow receiving member may be located upstream or downstream of the filter body. Alternatively, the flow receiving member may be located within the filter body itself. Still further, the flow receiving member may also function as an agitation member. With reference to FIG. 8, an alternative flow-receiving member 358 is provided as a threaded structure similar to an "Archimedes screw."

Figure 9:
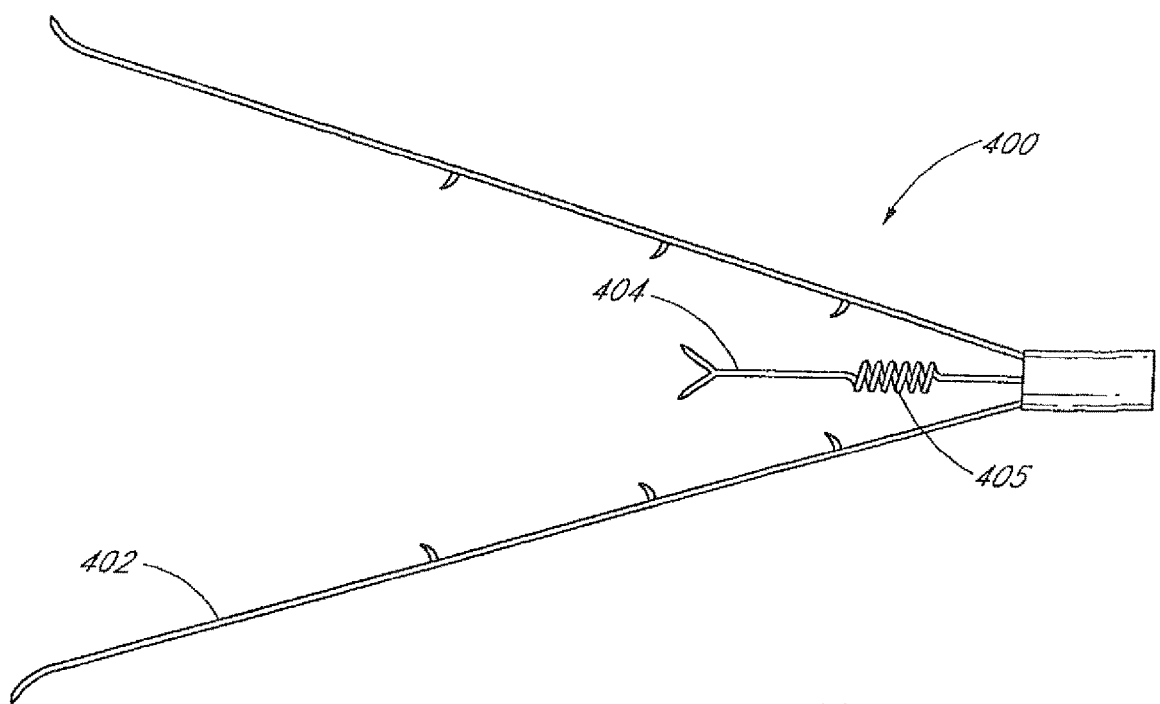
FIGS. 9 and 9A illustrate another alternative embodiment of a vascular filter device wherein a spring couples the agitation member to the filter body to allow limited longitudinal movement between the two.
Figure 9A:
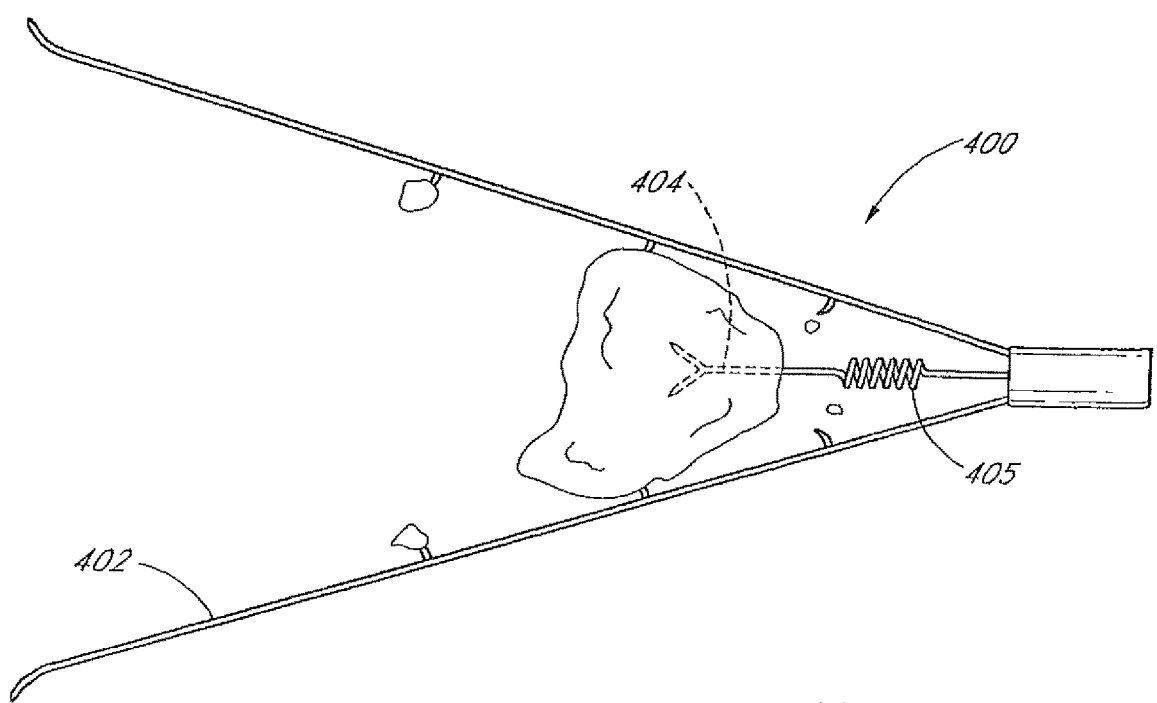

With reference now to FIG. 9, an alternative embodiment of a filter device 400 is illustrated wherein the agitation member 404 takes the form of a longitudinally moving body that is disposed within the interior volume of the filter body 402. In this embodiment, the agitation member is configured to penetrate and hold a captured embolus. At least one end of the agitation member is coupled to the filter body 402 by a deformable member, such as a spring 405. In this embodiment, the captured embolus is subjected to shear forces as changes in the flow rate of the blood cause the agitation to member to oscillate or pulse longitudinally within the filter body. FIG. 9A illustrates the filter device during use.

With reference now to FIG. 10, another alternative embodiment of a filter device 500 comprises an agitation member 504 including a plurality of vanes 510 that are substantially parallel with the wall of the filter body 502. In this embodiment, the flow receiving member and the agitation member are provided by the same structure. As the agitation member 504 rotates relative to the filter body 502, forces are exerted on a captured embolus for accelerating the dissolution of the embolus. A coupling member 520 is provided for maintaining the agitation member 504 in the proper alignment.

With reference now to FIG. 11, another alternative embodiment of a filter device 600 comprises an agitation member 604 that is capable of reversing direction. First and second vanes 610, 612 extend laterally across the opening to the filter body 602. Projections 622 are provided at the ends of the vanes, which are received by openings 620 along the rim of the filter body 602. The openings are configured such that projections 622 may rotate (i.e., readjust) within the openings. When the projections settle in a first position, the vanes 610, 612 are positioned to cause the agitation member to rotate in a first direction. When the projections 622 are turned 90 degrees and settle again, the vanes are then positioned to cause the rotating element to rotate in a second direction. After being implanted in a vessel, the vane positions may be readjusted by the patient's movements. Alternatively, the fluctuations in the blood flow may cause the vanes to readjust. In any event, the reversibility of the vanes advantageously reduces the possibility of clogging or jamming of the rotating element within the filter body.

In yet another alternative embodiment of a filter device, a mechanical clutch mechanism is provided such that the agitation member only rotates when a large clot is captured and contained within the filter. More particularly, when a clot is captured within the filter, hydrodynamic forces push the clot against the agitation member, thereby overcoming a biasing force and releasing the agitation member from engagement with the filter body such that it becomes free to rotate. In contrast, when there is no clot in the filter, the biasing force causes the agitation member to advance back into the rest position wherein the engagement members prevent the agitation member from rotating.

In other alternative embodiments, it is contemplated that the agitation member may be driven by an external source of power, rather than by the flow of blood through the vessel. With reference now to FIG. 12, in one preferred embodiment, a filter device 700 is configured to be powered by an elongate drive mechanism 750 that is advanceable through the patient's vasculature. The drive mechanism 750 is an elongate catheter body comprising an outer catheter 752 and an inner catheter 754. The inner catheter is configured to rotate within and relative to the outer catheter. The outer catheter is configured to remain rotationally fixed with respect to the filter body 702 and blood vessel. The distal end of the inner catheter 754 is formed with a recess 756 for mating with a shaft portion 706 of the agitation member 704. The outer catheter 752 is shaped for guiding the inner catheter into alignment with the shaft portion. With reference now to FIG. 12A, the outer catheter 752 mates with the hub 712 to hold the filter body 702 rotatably fixed while rotation of the inner catheter causes the agitation member to rotate within the filter body. The proximal end of the catheter body (not shown) extends outside of the patient and is connected to an external power source. Powered movement of the agitation member 704 may be used to macerate a captured embolus in a very quick and efficient manner at a high rotational velocity. When the maceration is complete, the catheter body may be withdrawn proximally such that is becomes decoupled from the shaft portion of the filter device. The catheter body may then be removed from the patient's vasculature.

Although the system is illustrated such that the elongate catheter body couples to the shaft portion from the downstream side (using access via the jugular vein), it will be appreciated that the system may be configured such that an elongate catheter or other drive mechanism may be advanceable from the upstream side (using access via the femoral vein) for driving the agitation mechanism. In another variation, it is contemplated that movement of the inner catheter is produced by manual movement of a control mechanism by a clinician. In various preferred embodiments, the control mechanism may take the form of a rotatable knob or a pull-wire. The pull wire may be used to produce relative linear movement of an agitation member for cutting, chopping and/or breaking up embolic material into smaller harmless pieces.

Using a vascular filter in combination with a powered (e.g., electrically, pneumatically, hydraulically, etc.) detachable mechanical drive mechanism provides a very efficient and effective method of emulsifying an embolus or other particle. In one advantage, distal embolization is minimized or eliminated because the embolus is macerated within the filter body. Furthermore, the agitation member is preferably disposed entirely within the filter body. Therefore, resulting damage to the inner wall of the vessel is minimized or eliminated. This provides a substantial advantage over existing mechanical thrombectomy systems wherein rotating blades or high velocity fluids can produce substantial damage to the vessel (i.e., endothelial denudation) and therefore presents a serious shortcoming.

Figure 13:
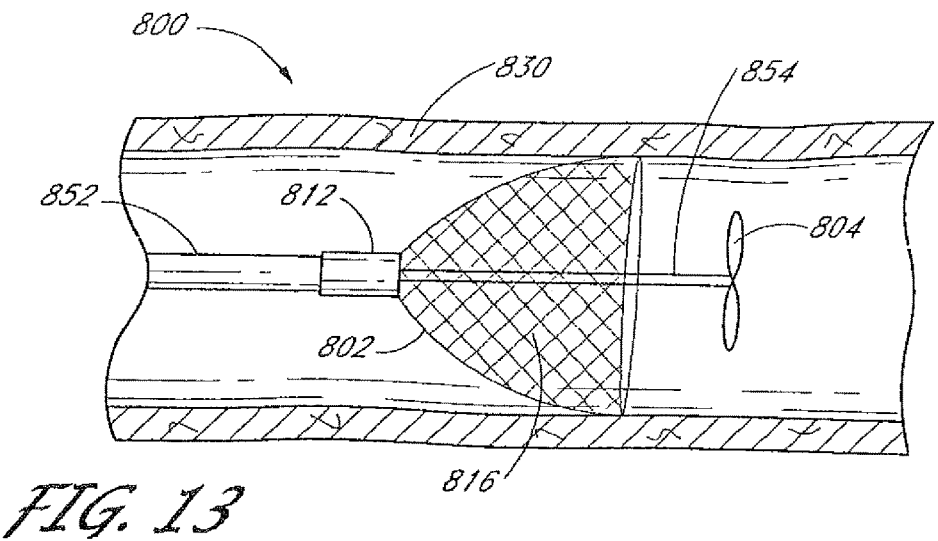
FIG. 13 illustrates another alternative embodiment of a vascular filter device wherein the elongate drive mechanism, filter body and agitation member are integrated into a single unit.

With reference to FIG. 13, in yet another alternative embodiment, a preferred configuration of the filter device 800 is well-suited for placement in a blood vessel 830 for use as a thrombectomy system. The filter device 800 comprises a filter body 802 and a powered rotatable agitation member 804 integrated together as a single unit. In this variation, the agitation member may be entirely or partially located within the interior volume 816 of the filter body 802. However, as illustrated in FIG. 13, the agitation member 804 is preferably longitudinally advanceable relative to the filter body 802. In this case, the agitation member is disposed along the distal end portion of a rotatable inner catheter 854, which is slidably and rotatably contained within a rotationally fixed outer catheter 852. The filter body 802 is disposed along the distal end portion of the outer catheter 852. A hub 812 may be provided at the junction between the outer catheter and the filter body. In one advantageous feature of this embodiment, the extendable agitation member may also be used as a guidewire during delivery of the device to a treatment site.

Figure 14:
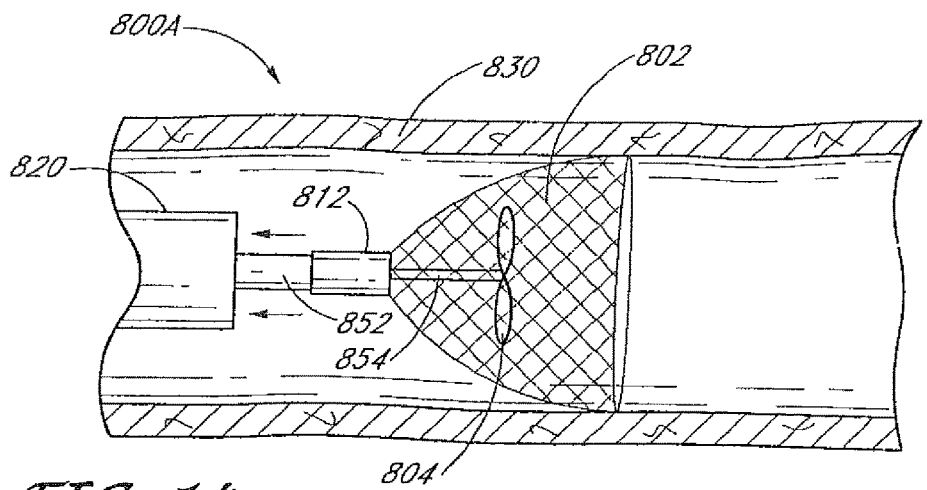
FIG. 14 illustrates the embodiment of FIG. 13 wherein the elongate drive mechanism is disposed within a lumen of a delivery sheath.

With reference now to FIG. 14, a variation of a filter device 800A which further comprises an aspiration catheter 820 for creating a fluid flow into the mouth of the filter body 802 and also for removing resulting particles from the vessel. The aspiration catheter may be used for aspirating fluid and particles from the vessel before, during or after maceration of an embolus. As illustrated, the aspiration catheter may be combined with the drive catheter into a single device. The aspiration catheter may further provide a delivery sheath for delivering the filter body to the treatment site.

Figure 15:
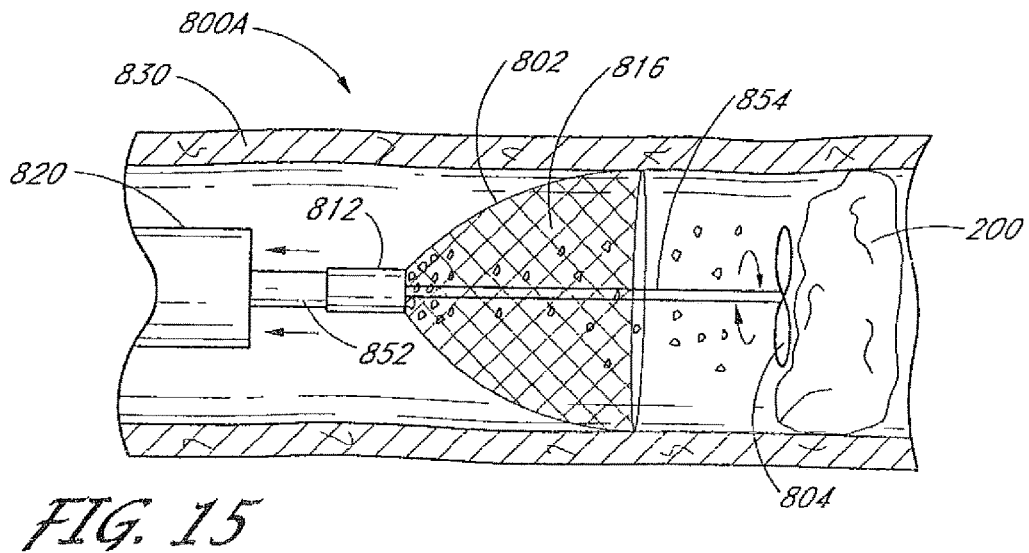
FIG. 15 illustrates the embodiment of FIG. 14 during use.

With reference now to FIG. 15, the filter device 800A of FIG. 14 is shown during use. After being advanced through a vessel 830 to a treatment site, negative pressure is applied at a proximal end of the aspiration catheter 820 to create a fluid flow into the mouth of the filter body 802. The inner catheter 854 may then be rotated for causing the agitation member 804 to rotate. While the agitation member is rotating, it may be advanced toward a thrombus 200 (or other particle) for macerating the thrombus and thereby removing the occlusion. During the maceration of the thrombus, resulting particles are drawn into the interior volume 816 of the filter body 802. Particles small enough to pass through the filter body are drawn into the aspiration catheter. As can be seen, this embodiment provides a very safe and effective mechanism for removing a thrombus from a blood vessel without any danger of distal embolization. It can further be seen that the filter helps center the agitation member such that the inner wall of the vessel is not damaged. At the end of the procedure, the inner catheter 854, outer catheter 852 and filter body 802 may all be withdrawn into the aspiration catheter 820 (or sheath) for safe removal from the patient's vasculature. It may be desirable to continue applying negative pressure along the proximal end of the aspiration catheter during removal such that the particles are not released from the filter.

With reference now to FIG. 16, an alternative filter body 852 is illustrated for further reducing the likelihood of particles escaping from the filter device. In this embodiment, the filter body 852 is formed with a plurality of stiffened members 854 which are hingedly attached to the hub 812. A flexible membrane 860 is disposed over the stiffened members. The stiffened members are biased into the open position to form a hemispherically-shaped filter body when in the non-constrained condition. With reference now to FIG. 16A, when the filter body 852 is withdrawn into an aspiration catheter 820 (or sheath), the stiffened members hingedly rotate (or flex) adjacent to the hub. Due to the curved shape of the stiffened members, when in the constrained condition, the distal ends of the stiffened member come together such that the distal opening of the filter body is nearly or completely closed, thereby preventing any particles from escaping. The membrane is configured to fold as the stiffened members come together.

With reference now to FIGS. 17A through 17C, an alternative agitation member 904 is illustrated wherein the diameter of the distal end is controllable. In this embodiment, the agitation member 904 may be disposed at the distal end of a rotatable inner catheter 906, similar to the device described above with reference to FIG. 15. However, in this embodiment, the agitation member comprises two flexible members 910, 912 disposed along the distal end of the inner catheter 906. In the illustrated embodiment, the flexible members further comprise weighted tips 920, 922. As the inner catheter 906 rotates, centrifugal forces cause the flexible members 910, 912 to flex outward away from the axis of rotation, thereby effectively increasing the diameter of the agitation member 904. Therefore, it can be seen that the diameter of the agitation member can be controlled by varying the rotational velocity $\omega$ (omega) of the inner catheter. For example, at $\omega_1$ the diameter of the agitation member is $D_1$, as shown in FIG. 17A. At $\omega_2$ the diameter of the agitation member is $D_2$, as shown in FIG. 17B. Finally, at $\omega_3$ the diameter of the agitation member is $D_3$, as shown in FIG. 17C.

Figure 18:
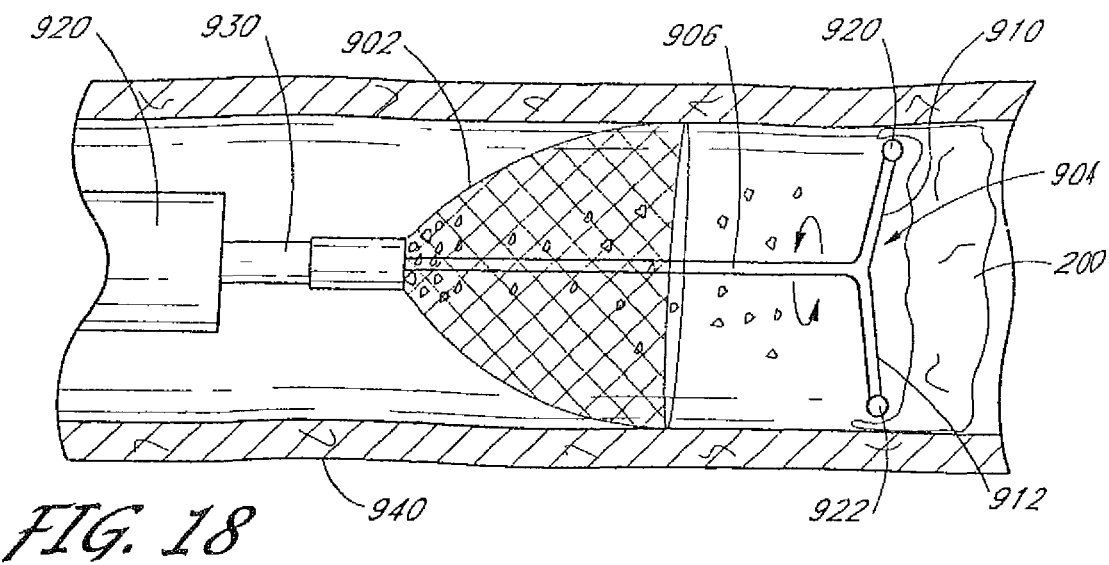
FIG. 18 illustrates the embodiment of FIGS. 17A-17C during use.

With reference now to FIG. 18, it can be seen that this feature advantageously allows the clinician to control the diameter of the agitation member to suit the diameter of the vessel 940 being treated. This allows for efficient thrombectomy without damaging the inner wall of the vessel. More particularly, the inner catheter 906 is advanced distally through an outer catheter 930 and out from the interior volume of the filter body 902. The inner catheter is rotated at a rotational velocity that causes its diameter to match the particular application. The rotating agitation member 904 may then be advanced for removing debris, such as an embolus 200, from the vessel 940. If desired, particles may be aspirated through the aspiration catheter 920.

Figure 19:
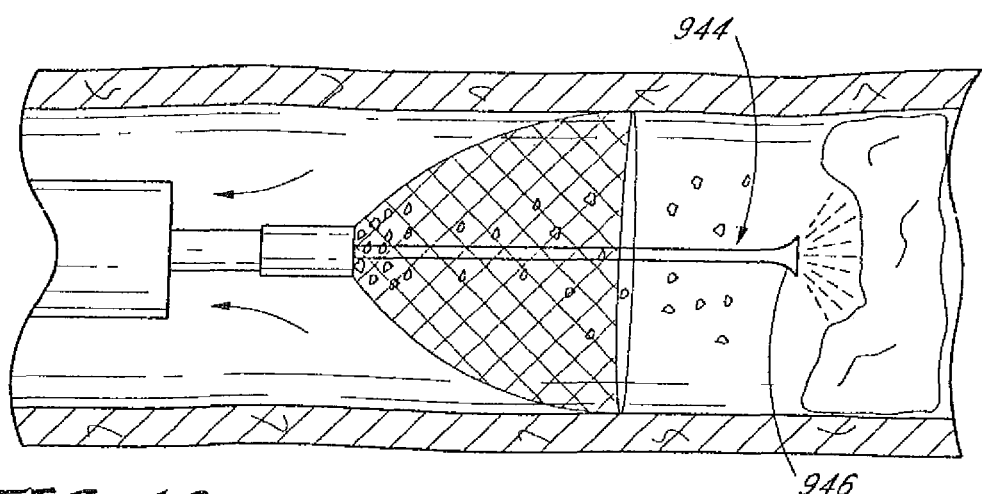
FIG. 19 illustrates another alternative embodiment of a vascular filter device wherein the agitation member is a nozzle for emitting pressurized fluid.

With reference now to FIG. 19, in yet another alternative embodiment of the filter device, an agitation member 944 comprises a nozzle or jet 946 for emitting a pressurized fluid flow. In the illustrated embodiment, this feature is used in combination with the inner catheter, outer catheter, filter body and aspiration catheter arrangement described above. However, in this embodiment, it is not necessary for the inner catheter to be rotatable. Rather, the inner catheter is configured with a fluid delivery lumen. If desired, the inner catheter may be configured to be deflectable, such as by using a pull wire of the type known in the art. The fluid delivered to the thrombus may be saline or any suitable fluid. In one variation, the fluid may comprise at least in part a thrombolytic drug for helping to break down the thrombus (or other particle).

Figure 20:
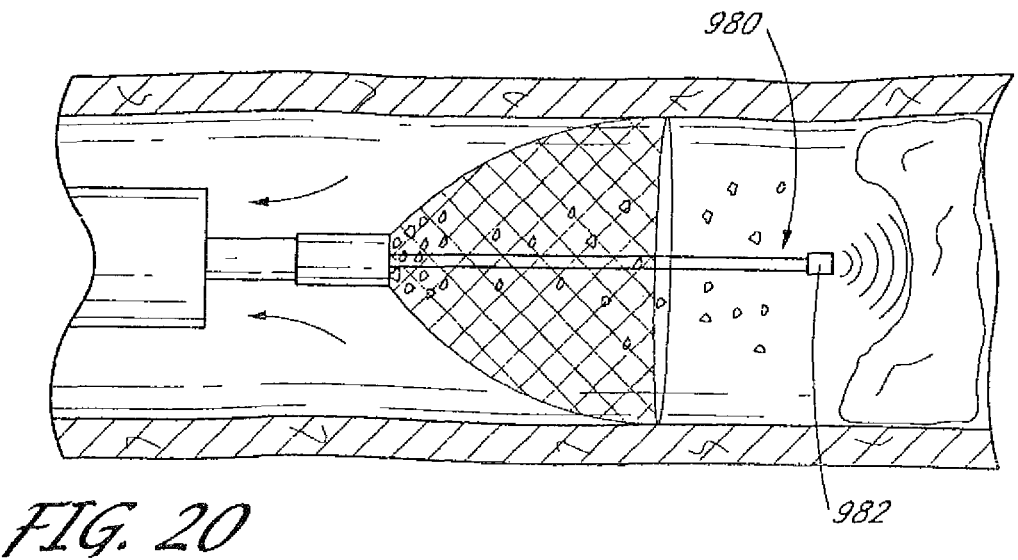
FIG. 20 illustrates another alternative embodiment of a vascular filter device wherein the agitation member is a vibrational mechanism.

With reference now to FIG. 20, in yet another alternative embodiment of the filter device, the agitation member 980 is configured to produce vibrational energy to help dissolve particles. In one variation, the agitation member 980 is capable of producing ultrasonic vibrations. The vibrations may be produced by movement of a mechanical mechanism, such as a vibrating ball. In another embodiment, the vibration may be produced by a transducer, such as a piezoelectric element 982 which oscillates in response to an electrical input. Ultrasonic vibrational energy may be used to quickly and efficiently dissolve (lyse) a clot, primarily by disrupting the fibrin matrix of the clot. The disruption is created by mechanical energy as well as by the formation of microbubbles caused by cavitation of fluids in the clot or in the surrounding blood or tissue. When ultrasound is used, the vibrations are provided in the range of about 19 to 45 kHz with a power input ranging from about 15 to 25 Watts. If desired, the delivery of vibrational (e.g., ultrasonic) vibrations to the clot may be accompanied by the delivery of thrombolytic drugs. The power required to produce the vibration of the agitation mechanism may be provided by electricity, such as through a wire in a catheter, through hydraulic pressure, or from an energy storage device contained within the filter device.

In yet another alternative embodiment of a filter device, an electric current may be delivered to the filter device for driving a motor located on the filter device. For example, when delivered temporarily, such as during an angioplasty procedure, an elongate wire may be provided for delivering an electrical current to an electric motor contained with the filter device, preferably along the hub. In various alternative embodiments, an electrical current may be applied to the agitation member or the filter body to help dissolve embolic material or other particles through electrical dissolution, rather than by mechanical maceration.

In yet another alternative embodiment of a filter device, an energy storage device, such as a battery, may be contained within the filter device for providing powered movement of the rotating member. In one variation, a control mechanism may be provided for turning the power on and off. In one example, the control mechanism may include a remote transmitter for sending a signal, such as by a RF signal, which turns a switch on and off. In this variation, the movable element only rotates when desired. In another embodiment, the filter device may further comprise a sensing mechanism, such as a pressure sensor of the type known in the art, for detecting when a clot is present in the filter. The sensing mechanism may be used to turn the agitation member on and off when necessary.

In yet another alternative embodiment, the agitation member is made, at least in part, of a ferro-magnetic material. In this embodiment, a variable magnetic field is used to produce movement (e.g., rotation) of the agitation member in the filter body by macerating particles. A sufficiently powerful magnetic field may be created outside of the patient's body by techniques known in the art.

In one alternative method of use, embodiments of the present invention are well-suited for use with patients undergoing total hip or knee replacement surgery. In this subset of patients, the risk of embolism is short-term and is typically limited to a definable period of time. Accordingly, for these patient's, it may be desirable to provide a temporary filter device coupled to a tether for facilitating removal thereof. The tether may take the form of a flexible elongate member coupled to the filter device in a manner as known in the art. During use, the tethered temporary filter device is preferably deployed from a catheter and is implanted in the infrarenal vena cava with the tether extending out of the puncture site in the neck (jugular) or groin (femoral), or buried subcutaneously within the soft tissues in the patient's neck. The tether remains coupled to the filter after deployment. When it is desirable to remove the filter, the tether may be used to manipulate the filter from a location outside the body. For example, the filter may be pulled proximally such that it is withdrawn into a catheter lumen. This embodiment may also be used for retrieving a filter during the initial deployment procedure. This is particularly useful when the initial deployment orientation is not desirable.

Although the improvements disclosed herein are primarily discussed in the context of use with a vascular filter for use in a blood vessel, the device described herein may also be used in a wide variety of other body lumens. In one alternative application, embodiments of the vascular filter may be used in the coronary arteries. The device may be delivered for use during an angioplasty procedure to help break down embolic debris released during the procedure. In one embodiment, the pulse of blood after removal of angioplasty balloon can be used to rotate the blades. Still further, the principles of the present invention may be applicable to any application, not necessarily biological, wherein it is desirable to capture and break apart particles.

While the foregoing detailed description has described several embodiments of the apparatus of the present invention, it is to be understood that the above description is illustrative only and is not limiting of the disclosed invention. It will be appreciated that the specific features of the invention can differ from those described above while remaining within the scope of the present invention. For example, the present invention is intended to include any filter device having a movable component within the interior volume for breaking apart captured particles and thereby providing a self-cleaning device. The movable component may be powered by the flow of a fluid through the filter or by an internal or external source of power.

What is claimed is:

1. A system for mechanically capturing and removing a thrombus from a blood vessel, comprising:
    a thrombectomy device adapted for percutaneous delivery into an occluded blood vessel, the thrombectomy device comprising:
        an inner catheter having a distal end portion adapted for penetrating and disrupting the thrombus,
        an aspiration catheter having a central lumen,
        an elongate catheter having a distal end portion, the elongate catheter sized to be slidably advanceable through the central lumen of the aspiration catheter, and
        a permeable, self-expanding filter body fixedly attached to the distal end portion of the elongate catheter, the self-expanding filter body having a tapered proximal end portion and an open distal end, the self-expanding filter body made from a nickel-titanium alloy and sized to conform to an inner wall of the occluded vessel;
    wherein the self-expanding filter body is permeable for capturing and holding particles resulting from the thrombus removal while allowing blood to pass through a wall of the self-expanding filter body and into the aspiration catheter and wherein the self-expanding filter body is collapsible for retrieval into the aspiration catheter after capturing the particles.

2. The system of claim 1, further comprising a thrombolytic drug for delivery to the thrombus.

3. The system of claim 1, wherein the self-expanding filter body further comprises a mesh structure.

4. The system of claim 1, wherein the inner catheter is a guidewire.

5. The system of claim 1, wherein a rotatable agitation member is provided along a distal end portion of the inner catheter for facilitating penetration into the thrombus.

6. The system of claim 1, further comprising a sheath for delivering the self-expanding filter body to the blood vessel and wherein the elongate catheter provides a pushing element for expelling the self-expanding filter body from a distal end of the sheath.

7. A system for mechanically capturing and removing a thrombus from a blood vessel, comprising:
    a thrombolytic drug; and
    a thrombectomy device adapted for treating the blood vessel, the thrombectomy device comprising:
        a guidewire having an agitation member disposed along a distal end portion, the agitation member adapted for penetrating and macerating the thrombus,
        an aspiration catheter having a central lumen,
        an elongate catheter having a distal end portion, and
        a self-expanding body having a proximal end securely fixed to the distal end portion of the elongate catheter, the self-expanding body extending distally beyond the distal end portion of the elongate catheter, the self-expanding body having a proximal end portion with a tapered shape and an open distal end sized to conform to an inner wall of the blood vessel while in an expanded configuration;
    wherein the self-expanding body is permeable for capturing particles resulting from the thrombus removal while allowing blood to pass through a wall of the self-expanding body and into the central lumen of the aspiration catheter and wherein the self-expanding body is collapsible for retrieving the particles into the central lumen of the aspiration catheter after the thrombolytic drug has been delivered to the thrombus.

8. The system of claim 7, wherein the thrombectomy device is suitable for reducing health problems associated with a stroke.

9. The system of claim 7, wherein the self-expanding body comprises an expandable stent structure for engagement with an inner wall of the blood vessel.

10. The system of claim 7, further comprising a sheath for delivering the self-expanding body to the blood vessel and wherein the elongate catheter provides a pushing element for expelling the self-expanding body from a distal end of the sheath.

11. A thrombus extraction system for mechanically capturing and removing a thrombus from a blood vessel of a patient, the thrombus extraction system comprising:
    an inner catheter having a length suitable for advancement through the blood vessel and into contact with the thrombus in the blood vessel, the inner catheter having an agitation member disposed along a distal end portion, the agitation member adapted for removal of the thrombus by manipulation of the inner catheter;
    an outer sheath sized for facilitating advancement of the inner catheter through the blood vessel, the outer sheath having an interior lumen and a distal end portion; and
    a self-expanding filter body having a proximal end portion with a tapered shape and an open distal end sized to conform to an inner wall of the blood vessel when in an expanded configuration, the self-expanding filter body sized for deployment in the blood vessel at a location distal to the distal end portion of the outer sheath;

wherein the outer sheath is adapted for applying negative pressure from a proximal end portion thereof and wherein the self-expanding filter body is shaped for capturing particles resulting from removal of the thrombus and wherein the self-expanding filter body has a permeable mesh structure for allowing blood to pass therethrough;

wherein the agitation member is collapsible for facilitating advancement toward the thrombus and wherein the agitation has an expanded diameter for removal of the thrombus.

12. The thrombus extraction system of claim 11, wherein the agitation member is sized for removing a thrombus from a femoral vein.

13. The thrombus extraction system of claim 11, wherein the self-expanding filter body is coupled to a distal end portion of an elongate catheter and wherein advancement of the elongate catheter causes the self-expanding filter body to deploy at a location distal to the distal end of the outer sheath.

14. A thrombus extraction system for removal of a vascular thrombus from a blood vessel of a patient, the thrombus extraction system comprising:
    an outer sheath having an interior lumen and a distal end;
    a self-expanding filter body having a proximal end portion with a tapered shape and an open distal end sized to conform to an inner wall of the blood vessel when deployed in the blood vessel, the self-expanding filter body sized for deployment at a location distal to the distal end of the outer sheath; and
    an inner catheter having a length suitable for advancement through the interior lumen of the outer sheath and through the self-expanding filter body, the inner catheter having an agitation member disposed along a distal end portion, the agitation member having an expanded diameter sized for contacting the thrombus, wherein the inner catheter and agitation member are longitudinally slidable for disrupting and removing the thrombus from the blood vessel;
    wherein the self-expanding filter body is adapted for capturing particles resulting from maceration of the thrombus and wherein the self-expanding filter body has a permeable mesh structure for allowing blood to pass therethrough.

15. The thrombus extraction system of claim 14, further comprising an elongate catheter for deploying the self-expanding filter body from the distal end of the sheath.

16. The thrombus extraction system of claim 14, further comprising a means for providing aspiration through the outer sheath.

17. A method of using the thrombus extraction system according to claim 14, comprising the steps of:
    inserting the outer sheath into the blood vessel;
    deploying the self-expanding filter body between the distal end of the outer sheath and the thrombus;
    advancing the agitation member through the interior lumen of the outer sheath and through the filter body, wherein the outer sheath and the filter body are maintained at a fixed location within the blood vessel during advancement of the agitation member; and
    contacting the thrombus with the agitation member for removing the thrombus from the blood vessel, wherein the thrombus is contacted distal to the filter body;
    wherein the blood vessel is a femoral vein and wherein the method is performed to treat deep vein thrombosis.

* * * * *